United States Patent [19]

Ganguly et al.

[11] 4,283,531

[45] Aug. 11, 1981

[54] SYNTHESIS OF β-LACTAMS HAVING A SUBSTITUTED HYDROXYMETHYLENE GROUP AT THE POSITION α TO THE LACTAM CARBONYL GROUP

[75] Inventors: Ashit K. Ganguly, Upper Montclair; Viyyoor M. Girijavallabhan, East Orange; Patricia Cavender, Lawrenceville; Olga Sarre, Verona; Stuart W. McCombie, West Orange, all of N.J.

[73] Assignee: Schering Corporation, Kenilworth, N.J.

[21] Appl. No.: 81,734

[22] Filed: Oct. 4, 1979

Related U.S. Application Data

[62] Division of Ser. No. 911,858, Jun. 2, 1978.

[51] Int. Cl.$^3$ .................. C07D 499/00; C07D 501/00
[52] U.S. Cl. ................. 544/30; 260/245.2 R; 260/245.2T; 260/245.3; 544/16; 544/26; 544/27; 424/246; 424/270; 424/271

[58] Field of Search .................. 544/16, 24, 30, 26, 544/27; 260/245.2, 245.3; 424/270, 271

[56] References Cited

U.S. PATENT DOCUMENTS

| 4,168,314 | 9/1979 | Christensen et al. | 424/270 |
| 4,172,144 | 10/1979 | Bosffard et al. | 260/245.2 |
| 4,172,895 | 10/1979 | Christensen et al. | 260/245.2 |

*Primary Examiner*—Nicholas S. Rizzo
*Attorney, Agent, or Firm*—Mary S. King; Barbara L. Renda

[57] ABSTRACT

β-Lactams having a substituted hydroxymethylene group at the position α to the lactam carbonyl group are prepared by reaction of an α-halo-β-lactam with zinc or zinc amalgam in an anhydrous aprotic medium to produce an intermediate which in situ reacts with an appropriate aldehyde or ketone.

Also described are novel penicillins and cephalosporins having useful antibacterial activity.

14 Claims, No Drawings

SYNTHESIS OF β-LACTAMS HAVING A SUBSTITUTED HYDROXYMETHYLENE GROUP AT THE POSITION α TO THE LACTAM CARBONYL GROUP

This is a division; of application Ser. No. 911,858, filed June 2, 1978.

This invention relates to a novel process and to novel compounds produced thereby.

More specifically, this invention relates to a process for preparing β-lactams having a substituted hydroxymethylene group at the position α to the lactam carbonyl group and to novel derivatives produced thereby.

In particular, this invention relates to a process for preparing penam and cepham derivatives.

The process aspect of this invention resides in the concept of preparing and isolating β-lactams having a substituted hydroxymethylene group at the position α to the lactam carbonyl group by reaction of an α-halo-β-lactam wherein the halo atom is located at the position that is α to the lactam carbonyl group with zinc or zinc amalgam in an anhydrous aprotic medium to produce an "intermediate" which reacts with an appropriate aldehyde or ketone.

More specifically, the process aspect of this invention resides in the concept of the process for preparation and isolation of a β-lactam having a substituted hydroxymethylene group at the position α to the lactam carbonyl group which comprises reaction of an α-halo-β-lactam with zinc or zinc amalgam in an anhydrous aprotic medium, in the presence of an appropriate aldehyde or ketone, and breaking the zinc complex by the addition of water or a buffer of pH of about 5-7. This process is accomplished without affecting the integrity of the β-lactam ring system.

The process of the present invention offers a one step synthesis from a halo-β-lactam starting material of the desired β-lactam having a substituted hydroxymethylene group at the position α to the lactam carbonyl group. The only previously described synthesis for compounds of this type is that of DiNinno, et. al., J. Org. Chem., 42, pp. 2960-2965. The DiNinno process involes the treatment of a solution of benzyl 6,6-dibromo-penicillanate with n-butyllithium or methylmagnesium bromide with excess acetaldehyde. It is then necessary to remove the bromine using a zinc-silver couple. The synthetic procedure described by DiNinno has also been applied to monobromopenicillanates. However, the yields were either low, or unwieldy low temperature conditions were required to produce the compound. The instant process provides good yields with simple reaction conditions utilizing zinc or zinc amalgam.

Zinc has previously been utilized as a reagent for the replacement of a halogen-carbon bond by a carbon-carbon bond. Usually, the halide is an α-halo ester or a vinylog of an α-halo ester. The zinc forms an intermediate with the bromoester, which reacts with the carbonyl compound to give an intermediate which may be hydrolyzed to the β-hydroxyester, which may undergo elimination to an olefin.

The process of this invention utilizes, instead of the α-halo ester, a β-lactam substituted at the α-position by a halogen atom. The process described herein most surprisingly effects the substitution of a carbon-carbon bond for the carbon-halogen bond. That a halo-β-lactam would react under such conditions is surprising due to the rather inert characteristics previously reported for such halo-β-lactams. While α-halo esters undergo facile reaction with an aldehyde or ketone in the presence of phosphine, β-lactams having a halogen at the α-position are unreactive under similar conditions. Similarly, the treatment of an α-halo ester with sodium azide results in the formation of the corresponding azide, while treatment of halo-β-lactam under such reaction conditions causes degradation of the β-lactam ring. Thus, treatment of a halo-β-lactam with zinc or zinc amalgam and an aldehyde and ketone resulting in the formation of the carbon-carbon bond while preserving the integrity of the β-lactam ring system is unobvious in view of the teachings of the art.

The halo substituent of the β-lactam utilized in the instant process may be either chloro, bromo or iodo. The starting materials wherein the halo-β-lactam is of the penicillin type are thus of the formula

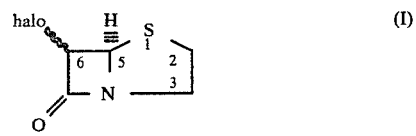

wherein the halo atom is chloro, bromo or iodo and the wavy line indicates either the α- or β-stereochemical configuration at the 6-position. Likewise, the starting materials wherein the halo-β-lactam is of the cephalosporin type are thus of the formula

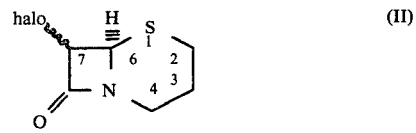

wherein the halo atom is chloro, bromo or iodo and the wavy line indicates either the α- or β-stereochemical configuration at the 7-position. Another appropriate starting material is an azetidine-2-one of the formula

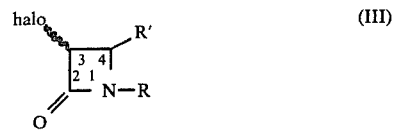

wherein the halo atom is chloro, bromo or iodo and the wavy line indicates either the α- or β-stereochemical configuration at the 3-position, and R and R' are appropriate substituted hydrocarbon groups.

Starting materials having the appropriate 6- or 7-halo substituent may be prepared from the appropriately substituted 6-amino- or 7-amino-β-lactam by reaction of the 6-amino- or 7-amino-β-lactam with sodium nitrite under the conditions described in J. Org. Chem., 27, 2668 (1962). Alternatively, these starting materials can be prepared from the 6- or 7-diazo compound by reaction with the appropriate hydrogen halide. Additional methodology for their preparation is described in Flynn, "Cephalosporins and Penicillins", pp. 101-105, Academic Press (1972).

The β-lactam starting material for the process of this invention preferably possesses the conventional penam ring system of the penicillins, e.g., IV

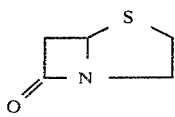 (IV)

or of the cephalosporins, e.g., V

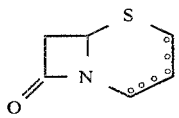 (V)

However, also utilizable in the present process are the numerous analogous β-lactam ring systems, such as VI, described in J. Chem. Soc. C., 2093 (1969)

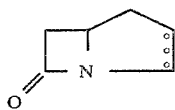 (VI)

wherein the dotted lines indicate the optional presence of a double bond; such as VII, described in *Can. J. Chem.* 55, 468 (1977), *Can. J. Chem.* 55, 484 (1977) and Belgian Patents 850,779 and 850,593

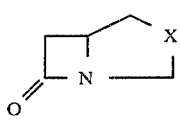 (VII)

wherein X is sulfur or oxygen; such as VIII, described in U.S. Pat. Nos. 4,068,075, 4,068,078, and 4,068,080

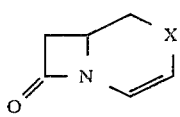 (VIII)

wherein X is nitrogen, sulfur or oxygen; such as IX and X, described in *Recent Advances in the Chemistry of β-Lactam Antibiotics*, Special Publication No. 28, Chapter 28, p. 213 (1977),

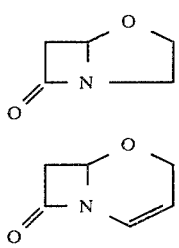

such as XI,

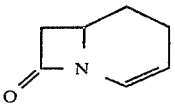 (XI)

such as XII, described in *J. Amer. Chem. Soc.* 88, 852 (1966),

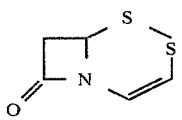 (XII)

such as XIII, described in *J. Amer. Chem. Soc.* 88, 852 (1966),

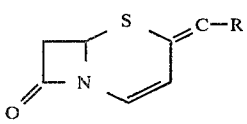 (XIII)

and those such as XIV,

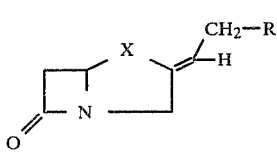 (XIV)

wherein X is nitrogen, oxygen or sulfur and R is alcohol, acyl ester, cyanide, sulfur, S—CH₃, nitrogen function or halogen.

Preferred starting materials for use in the reaction of this invention are: 6-halopenicillanic acid esters of the formula

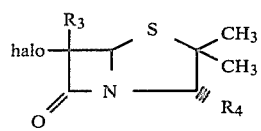 (XV)

wherein halo is a halogen selected from the group consisting of chlorine, bromine or iodine, $R_3$ is hydrogen or lower alkoxy, and $R_4$ is cyano or $COOR_{11}$ wherein $R_{11}$ is a readily removable ester-forming moiety;

7-halocephalosporanic acid esters of the formula

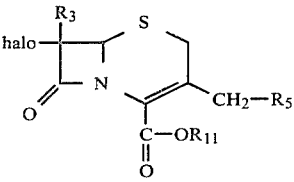 (XVI)

wherein halo, $R_3$ and $R_{11}$ are as hereinbefore defined, $R_5$ is hydrogen, lower alkanoyloxy, lower alkoxy, lower alkylthio, pyridinium,

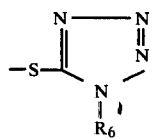

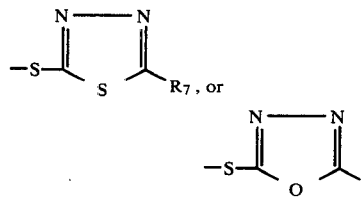

wherein $R_6$, $R_7$ and $R_8$ are hydrogen, lower alkyl, phenyl, lower alkylphenyl, halophenyl, hydroxyphenyl, lower alkoxyphenyl, or

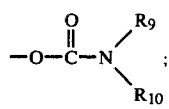

wherein $R_9$ and $R_{10}$ can be the same or different and are hydrogen or lower alkyl;

6-halopenicillanic acid esters of the formula

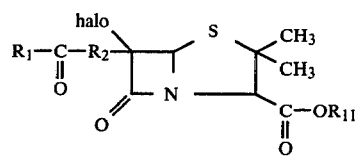 (XVII)

wherein halo and $R_{11}$ are as hereinbefore defined,

is an attached keto or aldehyde functional group, $R_2$ is a group of the formula

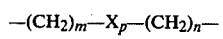

wherein X is O or S; m is 0–3; n is 0–3; p is 0–1; with the proviso that m+n+p is 3–5;

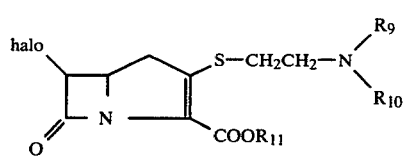 (XVIII)

wherein halo, $R_9$, $R_{10}$ and $R_{11}$ are as hereinbefore defined; and

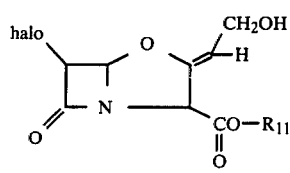 (XIX)

wherein halo and $R_{11}$ are as hereinfore defined.

The process of this invention involves reacting the halo-β-lactam with zinc or zinc amalgam to form a zinc-halo-β-lactam intermediate which goes on to react with aldehyde or ketone to form the final isolatable product.

This type of process is represented schematically as follows:

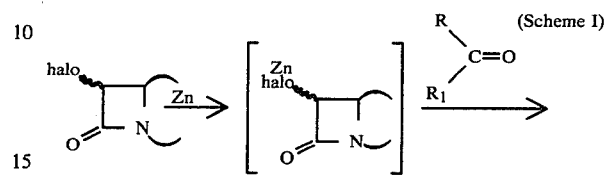 (Scheme I)

wherein

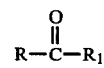

is the aldehyde or ketone and halo is chloro, bromo or iodo.

This process also proceeds when the aldehyde or ketone is part of the molecule reacted with the zinc or zinc amalgam resulting in an intramolecular reaction. This may be schematically represented by the following diagram:

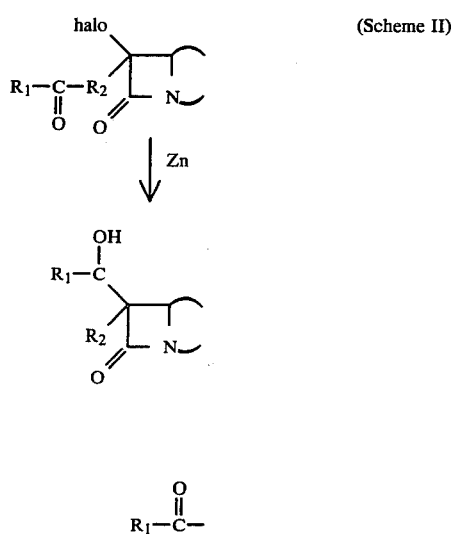 (Scheme II)

wherein

is an attached keto or aldehydo functional group, $R_2$ is a group of the formula

wherein X is O or S; m is 0–3; n is 0–3; p is 0–1; with the proviso that m+n+p is 3–5; and halo is chloro, bromo or iodo.

The process is preferably carried out under an inert atmosphere, e.g., nitrogen or argon to prevent undesirable side reactions. Atmospheric pressure affords reasonable reaction time for the process. However, pressure is generally not relevant except for gaseous aldehydes.

The process is necessarily carried out under anhydrous conditions to avoid conversion of the zinc-halo-β-lactam intermediate to the dehalo-β-lactam.

Solvents suitable for use in this process are any polar or non-polar aprotic organic solvent in which the halo-β-lactam starting material is soluble. Particularly useful solvents for the process are ethers such as ethyl ether, tetrahydrofuran, dioxane and diglyme; aromatic hydrocarbons such as benzene, toluene, xylene; and tertiary amides wuch as dimethylformamide and diethylformamide. Benzene and tetrahydrofuran are especially preferred solvents.

A solvent is not strictly necessary for the operation of the process of this invention, although its use is generally preferred. Thus, in the case where the aldehyde or ketone is a liquid in which the halo-β-lactam is soluble, the halo-β-lactam in the liquid aldehyde or ketone may be reacted with zinc or zinc dust without a solvent.

The reactants of this process are generally carried out at temperatures in the range of from about 0° C. to about 110° C. The reaction can also be carried out at the reflux temperature of the solvent used, with care to avoid temperatures above the boiling points of the aldehyde or ketone reactant. The reaction time depends upon the halo-β-lactam employed and the temperature at which the reaction is conducted. Reaction times of 2–12 hours are typical.

The zinc or zinc amalgam utilized in the process of this invention is activated in a conventional manner prior to its use in the reaction. Typical methods for accomplishing the activation may be found by reference to the following: Fieser and Fieser, *Reagents for Organic Synthesis*, Vol. 1, p. 1269 (1967); *Chem. Communications*, 269 (1973); *Synthesis*, 452 (1975) and "Accounts of Chemical Research," Vol. 10, 301 (1977).

The aldehydes and ketones utilizable in the present invention are those containing no functional group that would preferentially react with zinc or a zinc-halo-β-lactam intermediate over their oxo functionality, are not self-reacting, and do not generate a proton source substituent. Thus, aldehydes and ketones containing an unprotected hydroxy or amino group are not utilizable as such in this invention. The aldehydes and ketones may, however, contain these groups if the groups are suitably protected, e.g., with benzyl, benzhydryl, or tetrahydropyranyl groups, prior to reaction. Illustrative of groups that the aldehyde or ketone may contain are aliphatic groups of 1 to 20 carbon atoms, unsaturated straight- or branched-chain carbon groups of 1 to 20 carbon atoms, cycloalkyl groups of four to seven carbon atoms, heterocyclic groups not having free protons, e.g., tetrahydrofuran and thiophene groups, etc.

The halo-β-lactam starting materials must also be devoid of a proton source. Thus, for carboxy-, amino- and hydroxy- substituted compounds to be utilized in the process, the carboxy-, amino- and/or hydroxy-functional group must be protected from reaction by means of a suitable protecting group, e.g., benzyl or benzyloxy. Such groups as cyano, alkyl, and alkoxy are stable to the reaction conditions and thus may be present in the halo-β-lactam molecule without protecting groups.

A compound aspect of this invention resides in the concept of certain hydroxyalkyl-β-lactams and particularly the hydroxycycloalkyl-β-lactams which exhibit useful antibacterial activity. Most particularly, this aspect relates to compounds of the formulae:

wherein Y is a nitrogen, optionally lower alkyl, aryl or lower alkanoyl-substituted,
  oxygen,
  sulfur,
  oxygenated sulfur, or a lower alkyl, lower alkanoyl, or aryl-substituted or unsubstituted methylene group;
Z is selected from the group consisting of:

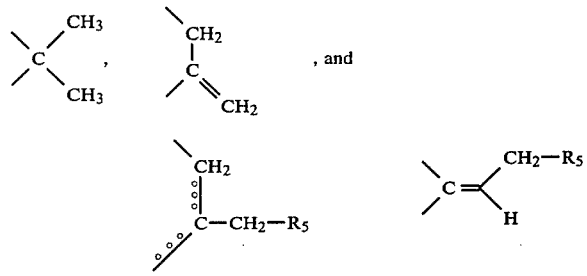

wherein the dotted lines indicate optional double bonds;
R₅ is hydrogen,
  lower alkanoyloxy,
  lower alkoxy,
  lower alkylthio,
  pyridinium,
  cyano,

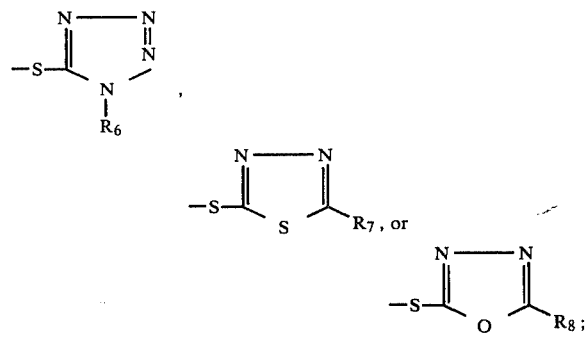

wherein $R_6$, $R_7$, and $R_8$ are hydrogen,
  lower alkyl,
  phenyl,
  lower alkylphenyl,
  halophenyl, hydroxyphenyl,
lower alkoxyphenyl, or

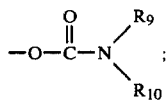

wherein $R_9$ and $R_{10}$ can be the same or different and are hydrogen, or lower alkyl; R and $R_1$, together with the carbon atom to which they are attached, is the carbon residue of an aldehyde or ketone which contains no functional group that would preferentially react with a zinc halo-β-lactam intermediate over the oxo functionality; $R_2$ is a group of the formula —(CH$_2$)$_m$—(X)$_p$—(CH$_2$)$_n$— wherein X is O or S;
m is 0–3;
p is 0–1;
n is 0–3; and
m+p+n is 3–5;
$R_3$ is hydrogen or
lower alkoxy; and
$R_4$ is cyano, or —COOR$_{11}$ wherein $R_{11}$ is a readily removable esterforming moiety, with the proviso that when $R_3$ is hydrogen, $R_4$ is —COOR$_{11}$, $R_{11}$ is benzyl or t-butyl, Y is nitrogen, and Z is

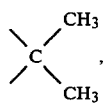

then R and $R_1$, together with the carbon atom to which they are attached, cannot be an acetaldehyde residue, and the pharmaceutically acceptable acid addition salts thereof.

These compounds are produced directly by the process of this invention.

Especially preferred compounds of formulae (XX) and (XXI) are those wherein Y is sulfur, Z is

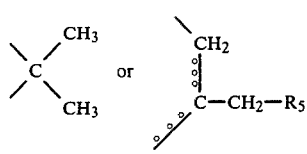

wherein $R_5$ is hydrogen, and $R_4$ is cyano. Reaction of the 6-bromo starting materials with various aldehydes and particularly substituted benzaldehydes produces compounds having a particularly desirable spectrum of antibacterial activity.

A further compound aspect of this invention relates to the preparation of compounds of the formulae:

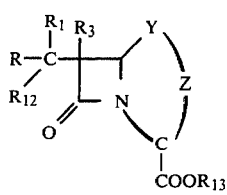

(XXII)

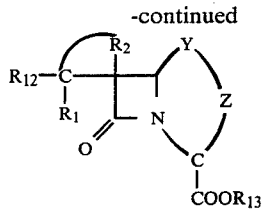

(XXIII)

wherein R, $R_1$, $R_2$, $R_3$, Y and Z are as hereinbefore defined; $R_{12}$ is hydroxy, lower alkoxy, formyloxy, lower alkanoyloxy, lower alkylsulfonyloxy, or a halogen atom; and $R_{13}$ is hydrogen, an alkali metal cation, acetoxymethyl, or a readily removable ester-forming moiety with the proviso that when $R_{12}$ is hydroxy, then $R_{13}$ is not a readily removable esterforming moiety, and the pharmaceutically acceptable acid addition salts thereof.

The lower alkyl groups referred to above contain 1 to 6 carbon atoms and are exemplified by methyl, ethyl, propyl, butyl, pentyl, hexyl, and the corresponding branched-chain isomers thereof.

The lower alkoxy groups referred to above likewise contain 1 to 6 carbon atoms and are exemplified by methoxy, ethoxy, propoxy, and the like.

Similarly, the lower alkanoyloxy groups contain from 2 to 7 carbon atoms and are typified by such groups as acetyloxy, propionyloxy and the corresponding branched-chain isomers thereof.

The "halogen atoms" encompassed by the term as used in this invention encompass fluorine, chlorine, bromine or iodine unless otherwise specified.

The term "lower alkylthio" refers to lower alkyl substituted thio groups such as methylthio, ethylthio, n-propylthio, isopropylthio, and the like.

"Lower alkylphenyl" likewise refers to phenyl groups substituted by one or two alkyl groups containing 1 to 6 carbon atoms. The term encompasses such groups as methylphenyl, ethylphenyl, n-propylphenyl, isopropylphenyl, dimethylphenyl, methylethylphenyl, and the like.

As used herein, the term "halophenyl" refers to mono- and dihalosubstituted phenyl groups such as mono- and dichlorophenyl, mono- and difluorophenyl and mono- and dibromophenyl groups.

The term "aryl" as used herein refers to phenyl substituted by one or more substituent groups selected from among chloro, bromo, fluoro, lower alkyl, hydroxy, nitro, amino, aminomethyl, lower monoalkylamino, lower dialkylamino, lower alkoxy and carboxy. Such aryl groups represented by $R_1$ can be, for example, 4-hydroxyphenyl, 3,4-dichlorophenyl, 2,6-dimethoxyphenyl, 4-methylphenyl, 2-fluorophenyl, 4-carboxyphenyl, 3-nitrophenyl, 4-aminophenyl, 3-aminophenyl, 4-dimethylaminophenyl, 4-aminomethylphenyl and 4-ethoxyphenyl.

The term "readily removable ester-forming moiety" refers to the commonly employed carboxylic acid protecting groups employed for protecting the $C_3$ carboxylic acid group of the penicillins and the $C_4$ carboxylic acid group of the cephalosporins. Representative of such groups are t-butyl, benzyl, benzhydryl, p-nitrobenzyl, 4-methoxybenzyl, 3,5-dimethoxybenzyl or tetrahydropyranyl and like cleavable ester moieties.

The compounds wherein $R_{13}$ is hydrogen are produced from the corresponding compounds wherein $R_{13}$ is a readily removable ester-forming moiety. A convenient method for accomplishing this reaction is by hydrogenation of the compound wherein $R_{13}$ is a readily removable ester-forming moiety sensitive to reductive cleavage in the presence of a palladium or palladium-on-carbon catalyst. Typical times are in the range of 6–48 hours and typical pressures in the range of atmospheric to 60 psi. For example, benzyl 6β-(α-hydroxy-o-fluorobenzyl)penicillanate is converted to 6β-(α-hydroxy-o-fluorobenzyl)penicillanic acid by hydrogenation for 40 hours at atmospheric pressure in the presence of a 30% palladium-on-carbon catalyst.

The compounds wherein $R_{13}$ is an alkali metal cation are produced from the corresponding compounds wherein $R_{13}$ is hydrogen by contact with one equivalent of an alkali metal salt in water at room temperature. For instance, 6β-(1-hydroxyethyl)-penicillanic acid is converted to the corresponding sodium salt by treatment with 1 equivalent of sodium bicarbonate in water.

The compounds wherein $R_{12}$ is formyloxy or lower alkanoyloxy are produced from the corresponding compounds wherein $R_{12}$ is hydroxy. The esterification proceeds conventionally utilizing an appropriate acid chloride, acid anhydride or activated amide in the presence of an acid acceptor. The acid acceptor may be an organic base such as pyridine or triethylamine or an inorganic base such as sodium or potassium hydroxide, or sodium or potassium bicarbonate. For instance, 6-(1-hydroxyethyl)-penicillanate may be converted to 6-(1-formyloxyethyl)penicillanate using dimethylformamide and tosyl chlorides or methanesulfonyl chloride; or to 6-(1-acetoxyethyl)penicillanate using acetic anhydride or acetylchloride and pyridine.

The compounds wherein $R_{12}$ is lower alkylsulfonoxy are produced from the corresponding compounds wherein $R_{12}$ is hydroxy and $R_{13}$ is a readily removed ester-forming moiety, by contacting with the appropriate alkylsulfonyl halide or alkylsulfonic anhydride in the presence of an acid acceptor. The $R_{13}$ group may then be removed as described hereinbefore.

The compounds wherein $R_{12}$ is halogen are prepared from the corresponding compounds wherein $R_{12}$ is an alkanesulfonyloxy group, preferably methanesulfonyloxy, and $R_{13}$ is a readily removable ester-forming moiety by contact with the appropriate halide ion. For instance, sodium iodide may be used to convert benzhydryl 6-(1-methanesulfonyloxyethyl)penicillanate to the corresponding benzhydryl 6-(1-iodoethyl)penicillanate. The $R_{13}$ protecting group may optionally be removed as hereinbefore described (other than by hydrogenation) to afford the corresponding free acid, i.e., 6-(1-iodoethyl)penicillanic acid.

The double bond of the cephem system may be isomerized by base to afford a mixture of the $\Delta^2$ and $\Delta^3$ cephems as products. The mixture is then separated by chromatography to afford the desired $\Delta^3$ compounds in a pure state.

Alternatively, the mixture is first oxidized to the sulfoxide according to the method of O'Connor and Lyness, *J. Amer. Chem. Soc.* 86, 3840 (1964). The sulfoxide is then reduced in the presence of an activating agent according to the method of Kaiser, et. al., *J. Org. Chem.* 35, 2430 (1970) to afford the $\Delta^3$ compounds in their pure state.

The compounds produced by the process of this invention possess antibacterial activity. Additionally, they are penicillinase inhibitors which may be used concommitantly with other penicillin-type antibiotics in infection therapy.

Thus, when tested in standardized microbiological assays the compounds of this invention exhibit activity vis-a-vis such organisms as *Staphylococcus epidermidis*, *Salmonella*, *Bacillus subtilis*, and *Pseudomonas aeruginosa* at test levels of 0.1 to 100 μcg/ml. Additionally, they show activity against such organims in the presence of penicillanase and cephalosporinase indicating a resistance to these enzymes. For instance, 6β-(p-benzyloxy-α-hydroxybenzyl)-2,2-dimethyl-3α-cyanopenam and 6α-(p-benzyloxy-α-hydroxybenzyl)-2,2-dimethyl-3α-cyanopenam show activity vis-a-vis *S. epidermidis* and *B. subtilis* at levels of 0.25 to 16 μcg/ml. The by-product, 2,2-dimethyl-3α-cyanopenam, exhibits activity vis-a-vis *S. epidermidis* (containing penicillanase) and *B. subtilis* (containing cephalosporinase) at levels of 0.1 to 50 μcg/ml. Additionally, this compound is a competitive β-lactamase inhibitor. Thus, as antibacterial agents these compounds are conventionally formulated for oral, intramuscular and intravenous therapy.

Thus, the present invention includes within its scope pharmaceutical compositions comprising the novel β-lactams of this invention with a compatible pharmaceutical carrier therefor.

The dosage administered of the β-lactams of this invention is dependent upon the age and weight of the animal species being treated, the mode of administration, and the type and severity of bacterial infection being prevented or reduced. Typically, the dosage administered per day will be in the range of 100–5000 mg with 500–1000 mg being preferred.

For oral administration, the compounds of this invention may be formulated in the form of tablets, capsules, elixirs or the like. For parenteral administration they may be formulated into solutions or suspensions for intramuscular injection.

The following examples describe in detail the process of the present invention and the compounds produced therefrom. It will be apparent to those skilled in the art that many modifications, both of materials and methods, may be practiced without departing from the spirit and scope of the invention.

PREPARATION 1

A solution of 11.0 g benzyl 6-diazopenicillanate 1β-oxide and 9 g 3-buten-1-ol in 120 ml dichloromethane is stirred with ice-cooling, and 7.5 g N-bromosuccinimide is added in portions over a 5 minute period. After stirring for 18 minutes at room temperature, the solution is washed successively with water, aqueous sodium sulfite and aqueous sodium bicarbonate. After drying over anhydrous magnesium sulfate and removal of the solvents in vacuo, the residue is chromatographed on silica gel by eluting rapidly with benzene followed by 10% ethyl acetate in benzene. The product, benzyl 6α-(3-buten-1-yloxy)-6β-bromopenicillanate 1β-oxide, is isolated as a yellow oil. This compound is represented by the formula:

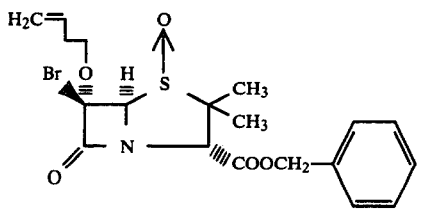

PREPARATION 2

A solution of 9.2 g benzyl 6α-(3-buten-1-yloxy)-6β-bromopenicillanate 1β-oxide in 70 ml dry dimethylformamide is cooled to 5° C. Then, 2.4 ml phosphorus tribromide is added dropwise and the mixture is stirred for 1 hour at room temperature. The mixture is added to ice water and extracted with ethyl ether. The organic phase is separated and washed successively with water, sodium bicarbonate solution and saturated sodium chloride solution. After drying over anhydrous magnesium sulfate, the solvents are removed by evaporation. The crude product is chromatographed rapidly on 150 g silica gel using 1:1 dichloromethane-hexane as the eluant, affording benzyl 6β-bromo-6α-(3-buten-1-yloxy)-penicillanate, as a yellow oil, and having the following formula:

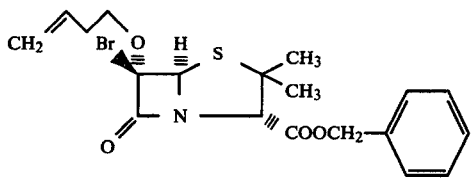

PREPARATION 3

A solution of 6.3 g benzyl 6β-bromo-6α-(3-buten-1-yloxy)penicillanate in 80 ml dichloromethane and 30 ml methanol is cooled to −20° C. and ozonized oxygen is introduced until the starting material is consumed (as determined by t.l.c.). Then, 10 ml dimethyl sulfide is added, the resultant solution is brought to room temperature, and washed twice with 100 ml portions of water. The aqueous phases are combined and extracted with 50 ml dichloromethane. The dichloromethane extracts are combined with the original organic phase and dried over anhydrous magnesium sulfate. The dried solution is evaporated in vacuo at room temperature to leave benzyl 6α-(3-oxopropoxy)-6β-bromopenicillanate as an oil.

EXAMPLE 1

To a solution of 500 mg methyl 6α-bromopenicillanate in 7 ml anhydrous acetaldehyde is added active zinc dust with constant stirring at 20° C. The progress of the reaction is monitored by thin layer chromatography using a 10% acetone in benzene solvent system. Upon completion of the reaction, the zinc is removed by filtration, and the mixture is diluted with 50 ml ethyl acetate and washed with phosphate buffer (10 ml) of pH 5 to remove the zinc salts. After drying the solution over anhydrous sodium sulfate and removing the solvent under vacuum, the product is chromatographed through silica using 3% acetone in benzene as eluant. The initial fraction is discarded. The following fractions afford, in 80:20 ratio, methyl 6β-(1-hydroxyethyl)-penicillanate and methyl 6α-(1-hydroxyethyl)penicillanate. The 6β compound has the following formula:

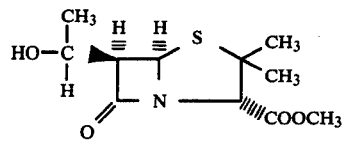

EXAMPLE 2

A solution of 500 mg methyl 6-bromopenicillanate in 25 ml dry benzene containing 1 ml benzaldehyde and 2 g active zinc dust is refluxed under a nitrogen atmosphere with vigorous stirring for approximately 6 hours. Upon termination of the refluxing, the reaction mixture is diluted with 50 ml ethyl acetate and washed with a phosphate buffer of pH 5. The solution is dried over anhydrous sodium sulfate and the solvents are removed under vacuum. The products were separated by preparation thin layer chromatography using multiple elutions with 3% acetone in chloroform to afford, in a 6:1 ratio, methyl 6α-(α-hydroxybenzyl)penicillanate and methyl 6β-(α-hydroxybenzyl)penicillanate.

EXAMPLE 3

To a solution of 8 g benzhydryl 6α-bromopenicillanate in 150 ml dry tetrahydrofuran is added 35 ml dry acetaldehyde, followed by 13 g active zinc. The mixture is then stirred very vigorously for 2½ hours. Upon completion of the reaction, the mixture is taken up in 500 ml ethyl ether and washed with phosphate buffer of pH 5. The solution is dried over anhydrous sodium sulfate and the solvents are removed under vacuum. The resultant foamy solid is chromatographed through silica gel using 5% acetone in benzene to afford a major amount of benzhydryl 6β-(1-hydroxyethyl)penicillanate and a minor amount of benzhydryl 6α-(1-hydroxyethyl)-penicillanate.

EXAMPLE 4

To a solution of 1.5 g benzhydryl 6α-bromopenicillanate in 20 ml dry tetrahydrofuran is added 3 ml o-fluorobenzaldehyde, followed by 2.5 g active zinc. After stirring vigorously for 4 hours, the zinc is filtered from reaction mixture and the mixture is taken up in 200 ml ethyl acetate and washed first with phosphate buffer of pH 5 and then with 15 ml of 1% aqueous sodium bicarbonate. After drying the solution over anhydrous sodium sulfate and removal of the solvents under vacuum, the product is chromatographed utilizing 5% acetone in toluene to afford benzhydryl 6β-(o-fluoro-α-hydroxybenzyl)-penicillanate and benzhydryl 6α-(o-fluoro-α-hydroxybenzyl)penicillanate. The 6β compound has the following formula:

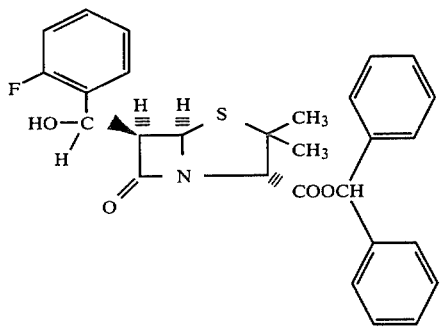

When p-dimethylaminobenzaldehyde is substituted for the o-fluorobenzaldehyde in the above procedure, there is obtained benzhydryl 6-(p-dimethylamino-α-hydroxybenzyl)penicillanate.

EXAMPLE 5

To a solution of 2.5 g benzhydryl 6α-bromopenicillanate in 35 ml dry tetrahydrofuran is added 5 ml cinnamaldehyde and 5.2 g active zinc. The resultant solution is stirred vigorously for 12 hours in the presence of a catalytic amount of copper (II) chloride. The mixture is then taken up in 200 ml ethyl acetate and washed with phosphate buffer of pH 5. The solution is dried over anhydrous sodium sulfate and the solvents removed under vacuum. The excess cinnamaldehyde is removed by using high vacuum and the product is chromatographed using 5% acetone in benzene to afford benzhydryl 6β-(1-hydroxy-3-phenylprop-2-enyl) penicillanate and benzhydryl 6α-(1-hydroxy-3-phenylprop-2-enyl) penicillanate. The 6β compound has the formula:

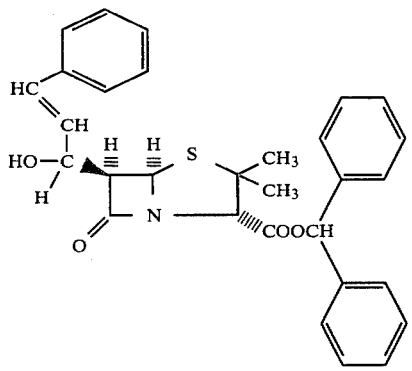

EXAMPLE 6

A solution of 1 g of benzyl 7α-bromo-3-methylenecephalosporinate in 50 ml dry tetrahydrofuran is stirred with 5 ml dry acetaldehyde and 5 g active zinc under a nitrogen atmosphere for 1.5 hours. The reaction mixture is then filtered, diluted with 100 ml ethyl acetate and washed with phosphate buffer of pH 5. The solution is dried over hydrous sodium sulfate and the solvents removed under vacuum. NMR spectra show that the exocyclic methylene group is intact. Chromatography on thin layer chromatography plates using 5% acetone in benzene affords benzyl 7β-(1-hydroxyethyl)-3-methylenecephalosporinate and benzyl 7α-(1-hydroxyethyl)-3-methylenecephalosporinate. Each of the two compounds is then independently treated with 500 mg triethylamine in 20 ml ethyl acetate to shift the double bond to conjugation. The solvents are removed under high vacuum to afford, respectively, benzyl 7β-(1-hydroxyethyl)desacetoxy-Δ² or Δ³-cephalosporinate and benzyl 7α-(1-hydroxyethyl)desacetoxy-Δ² or Δ³-cephalosporinate.

EXAMPLE 7

A solution of 1.6 g benzhydryl 7α-bromocephalosporinate in 50 ml dry tetrahydrofuran is stirred with 3.2 g active zinc dust and 8 ml acetaldehyde for 20 hours. The reaction mixture is then filtered, diluted with ethyl acetate and washed with phosphate buffer of pH 5. The solution is dried over anhydrous sodium sulfate and the solvents are removed under vacuum. Chromatography of the resultant product affords benzhydryl 7β- and 7α-(1-hydroxyethyl)cephalosporinate as well as the corresponding 7β- and 7α-Δ² compounds.

EXAMPLE 8

To a solution of 3.0 g benzyl 6β-bromo-6α-methoxypenicillanate in 35 ml dry tetrahydrofuran and 10 ml dry acetaldehyde is added 2 g zinc dust. The mixture is stirred at 25° C. under a nitrogen atmosphere for 2 hours. The excess zinc is removed by filtration and washed with ethyl acetate and the filtrates washed first with dilute hydrochloric acid and then sodium bicarbonate solution. After drying over anhydrous magnesium sulfate, the solvents are removed in vacuo and the residue chromatographed on silica gel, eluting with chloroform containing 0.5% methanol. The appropriate fractions containing the desired product ($F_f \approx 0.5$ on silica gel in 1% methanolchloroform) are combined and rechromatographed on silica using 7% ethyl acetate in benzene. Removal of the solvents and recrystallization from ether-hexane give the desired product, benzyl 6-(1-hydroxyethyl)-6-methoxypenicillanate, as a white solid melting at 86°–88° C. and having the following formula:

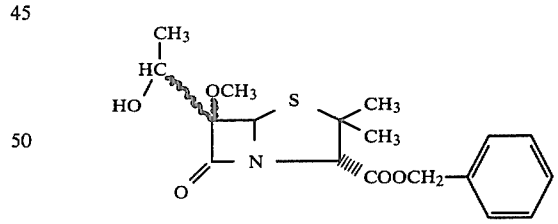

wherein the wavy lines indicate the α- or β-configuration.

EXAMPLE 9

To a solution of 0.3 g 2,2-dimethyl-3α-cyano-6α-bromopenam in 6 ml anhydrous tetrahydrofuran and 1.68 ml anhydrous acetaldehyde is added 1.0 active zinc dust. The reaction mixture is stirred vigorously at room temperature for 4 hours where upon 1 ml phosphate buffer of pH 5 is added. After stirring a few minutes, the reaction mixture is diluted with ethyl acetate, filtered and the organic phase washed once with brine. After drying over anhydrous sodium sulfate, the residue is chromatographed on silica gel, using 3% acetone in benzene as eluant. Thus isolated, in a 2:1 ratio, are 2,2-dimethyl-3α-cyano-6β-(1-hydroxyethyl)penam and 2,2-dimethyl-3α-cyano-6α-(1-hydroxyethyl)penam.

A by-product of this reaction, 2,2-dimethyl-3α-cyanopenam, is also isolated in a minor amount.

EXAMPLE 10

To a solution of 60 mg 2,2-dimethyl-3α-cyano-6α-bromopenam and 3 drops benzaldehyde in 1 ml dry tetrahydrofuran is added 1 g zinc dust. The reaction mixture is stirred at room temperature for about 12 hours under nitrogen atmosphere. A few drops of phosphate buffer of pH 5 is added and then the mixture is diluted with ethyl acetate. The zinc dust is filtered and washed with ethyl acetate. The ethyl acetate extracts are combined, washed with aqueous sodium chloride, and dried over anhydrous sodium sulfate. Chromatography of the mixture on silica gel using 10% acetone in chloroform affords in an 11:6 ratio, 2,2-dimethyl-3α-cyano-6α-(α-hydroxybenzyl)penam and 2,2-dimethyl-3α-cyano-6β-(α-hydroxybenzyl)penam.

EXAMPLE 11

A solution of 100 mg 2,2-dimethyl-3α-cyano-6α-bromopenam in 40 ml dry tetrahydrofuran is stirred with 60 mg p-dimethylaminobenzaldehyde and 500 mg zinc for about 12 hours at room temperature. The reaction mixture is then diluted in ethyl acetate, washed with aqueous sodium chloride and dried over anhydrous sodium sulfate. Chromatography of the mixture on silica gel affords, in 11:1 ratio, 2,2-dimethyl-3α-cyano-6α-(p-dimethylamino-α-hydroxybenzyl)penam and 2,2-dimethyl-3α-cyano-6β-(p-dimethylamino-α-hydroxybenzyl)penam. The 6α-compound has the following formula:

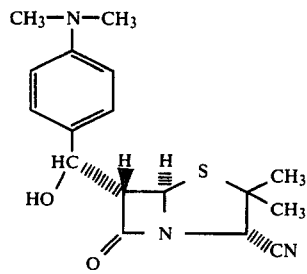

Utilizing 7α-bromo-4-cyano-3-cephem in the above procedure similarly affords 7α-(p-dimethylamino-α-hydroxybenzyl)-4-cyano-3-cephem.

EXAMPLE 12

Utilizing substantially the procedure detailed in Example 11, 2,2-dimethyl-3α-cyano-6α-bromopenam is reacted with p-benzyloxybenzaldehyde to afford 2,2-dimethyl-3α-cyano-6α-(p-benzyloxy-α-hydroxybenzyl)penam and 2,2-dimethyl-3α-cyano-6β-(p-benzyloxy-α-hydroxybenzyl)penam. These compounds are represented by the following structural formula wherein the wavy line represents the α- or β-configuration.

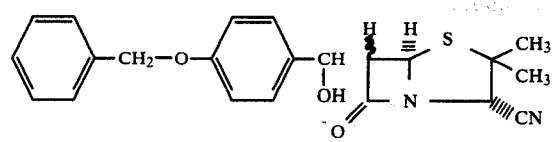

EXAMPLE 13

A solution of 5.8 g benzyl 6α-(3-oxopropoxy)-6β-bromopenicillanate in 100 ml dry tetrahydrofuran is stirred under argon for 20 hours with 25 g zinc dust. The mixture is then diluted with 200 ml ethyl acetate and 10 ml water, and the solids filtered and washed with ethyl acetate. The filtrate is washed with water, dried over anhydrous magnesium sulfate and evaporated. The residue is chromatographed on 80 g silica gel eluting rapidly with dichloromethane followed by 5% ethyl acetate in dichloromethane. The apropriate eluates are combined and evaporated to give a mixture of benzyl spiro-[3'-hydroxy oxacyclopentyl]-2',6α-penicillanate and benzyl spiro[3'-hydroxy oxacyclopentyl]-2',6β-penicillanate.

Separation is effected by preparative thin layer chromatography on 0.1 cm layer plates, using two elutions with 3:2 v/v hexane:ethyl acetate. The bands are removed, the products are eluted using ethyl acetate. After evaporation, the residues are recrystallized from ether-hexane to afford the two compounds as white prisms, m.p. 105°–106° C. and as white prisms melting at 113°–115° C. These may be represented by the formula

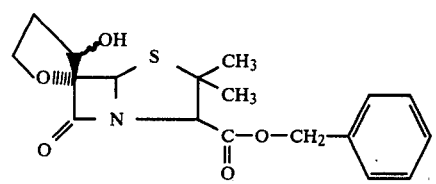

wherein the wavy line indicates the α- or β-configuration.

EXAMPLE 14

A solution of 150 mg of benzhydryl 6β-(1-hydroxyethyl) penicillanate in 25 ml ethanol is hydrogenolysed in the presence of a 10% palladium-on-carbon catalyst at 20 psi. After 24 hours, the solution is filtered to remove the catalyst and the solvent is evaporated. The resultant crystals, 6β-(1-hydroxyethyl)penicillanic acid, are treated with one equivalent of sodium bicarbonate in water. Freeze drying thus affords sodium 6β-(1-hydroxyethyl)penicillanate.

EXAMPLE 15

A solution of 100 mg benzyl 7-(1-hydroxyethyl)-desacetoxy-Δ³-cephalosporinate in 20 ml ethanol is hydrogenated at 30 psi using a 10% palladium-on-carbon catalyst for 30 hours. The reaction mixture is then filtered to remove the catalyst and the solvent removed under vacuum to afford 7-(1-hydroxyethyl)desacetoxy-Δ³-cephalosporanic acid. This product is then treated with one equivalent of sodium bicarbonate and lyophilized to yield sodium 7-(1-hydroxyethyl)desacetoxy-Δ³- cephalosporanic acid having the following structural formula

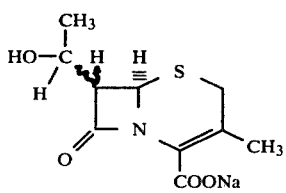

wherein the wavy line indicates the α- or β-configuration.

EXAMPLE 16

A solution of 38 mg of benzhydryl 6β-(o-fluoro-α-hydroxybenzyl)penicillanate in 10 ml ethanol containing 2 mg N-methylglucamine is hydrogenated for 40 hours using a 30% palladium-on-carbon catalyst and atmospheric pressure. The reaction mixture is then filtered, the solvent removed under vacuum, and the resultant product washed with petroleum ether to remove any excess diphenylmethane. Thus produced is 6β-(o-fluoro-α-hydroxybenzyl)penicillanic acid.

EXAMPLE 17

A solution of 150 mg benzhydryl 6-(1-hydroxyethyl)-penicillanate in 5 ml dry dimethylformamide is treated with 200 mg tosyl chloride followed by 200 mg triethylamine. After 12 hours, the reaction mixture is dissolved in ethyl acetate and then washed successively with water, 5% aqueous phosphoric acid, 1% aqueous sodium bicarbonate, and brine. After the solution is dried over anhydrous sodium sulfate, the solvents are removed under vacuum to afford, as a foam, benzhydryl 6-(1-formyloxyethyl)penicillanate.

EXAMPLE 18

A solution of 411 mg benzhydryl 6-(1-hydroxyethyl)-penicillanate in 10 ml dry acetonitrile is treated with 150 mg dry pyridine and 250 mg methanesulfonic anhydride. When the starting material is no longer present (as determined by thin layer chromatography), the reaction mixture is diluted with 50 ml ethyl acetate and washed first with 3 ml of 5% aqueous phosphoric acid, subsequently with 15 ml of 2% aqueous sodium bicarbonate and finally with brine. The resultant solution is dried over anhydrous sodium sulfate and the solvents removed under vacuum to afford as a foamy solid, benzhydryl 6-(1-methanesulfonyloxyethyl)penicillanate.

EXAMPLE 19

A solution of 50 mg of benzhydryl 6-(1-methanesulfonyloxyethyl)penicillanate in 5 ml dry acetone is kept in the presence of 200 mg sodium iodide for 5 days. The acetone is then removed under vacuum and the residue is dissolved in 50 ml ethyl ether. The ether solution is washed first with water and then with aqueous sodium thiosulfate. After drying over anhydrous sodium sulfate, the solvent is removed under vacuum to afford, as a white solid, benzhydryl 6-(1-iodoethyl)penicillanate, having the formula

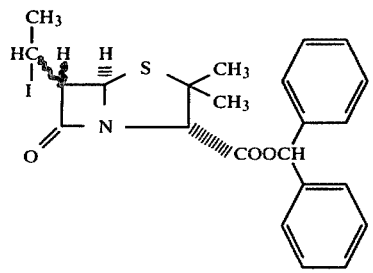

EXAMPLE 20

A solution of 0.6 g benzyl 6-(1-hydroxyethyl)-6-methoxypenicillanate in 30 ml ethanol and 10 ml water containing 0.2 g sodium bicarbonate is shaken for 20 hours with 1 g 10% palladium-on-charcoal catalyst at 60 psi. The mixture is then filtered, washed with aqueous ethanol and evaporated in vacuo to remove most of the ethanol. The residual aqueous solution is extracted once with ether and the extract discarded. The aqueous phase is acidified to about pH 1.5 with phosphoric acid and then extracted 5 times with 50 ml portions of dichloromethane. The dichloromethane extracts are combined, dried over anhydrous magnesium sulfate and evaporated. The residue is crystallized from ether-hexane to afford 6-(1-hydroxyethyl)-6-methoxypenicillanic acid as a white, crystalline solid melting at 201°–204° C. with decomposition. To an ethanol solution contaning the free acid is added 1 ml of a 0.6 M dichloromethane solution of potassium 2-ethylhexanoate followed by 30 ml hexane. The precipitate is filtered, washed with hexane and dried in vacuo at 50° C. to afford, as a white powder, potassium 6-(1-hydroxyethyl)-6-methoxypenicillanate.

EXAMPLE 21

Activated mossy zinc (500 mg) and zinc dust (100 mg) are added to a solution of 2,2-dimethyl-3α-cyano-6α-bromopenam (522 mg, 2 mmol) and p-(2-tetrahydropyranyloxy)benzaldehyde (750 mg, 3.75 mmol) prepared according to E. Piers, W. deWaal and R. W. Britton, *J. Am. Chem. Soc.*, 93, 5113 (1971) in 1 ml of dry tetrahydrofuran. After stirring vigorously at 50° for 3 hrs., the mixture is allowed to cool and 1 ml of pH 5 phosphate buffer is added. After standing for 10 min., the solids are removed by filtration and washed thoroughly with ethyl acetate. The filtrate is extracted with ethyl acetate. The combined extracts are washed with phosphate buffer and saturated sodium chloride, dried with sodium sulfate and the solvents removed by evaporation. The crude material is purified by chromatography on 60 g of silica gel using 40% acetone/chloroform as eluant to afford 2,2-dimethyl-3α-cyanopenam as a by-product melting at 73°–75° C. and a mixture of 2,2-dimethyl-3α-cyano-6α-[p-(2-tetrahydropyranyloxy)-α-hydroxybenzyl]penam and 2,2-dimethyl-3α-cyano-6β-[p-(2-tetrahydropyranyloxy)-α-hydroxybenzyl]penam. Separation of the 6α- and 6β-compounds is effected by PLC (10% acetone/toluene; two developments) providing the individual 6α- and 6β-compounds.

EXAMPLE 22

2,2-Dimethyl-3α-cyano-6α-[p-(2-tetrahydropyranyloxy)-α-hydroxybenzyl]penam (45 mg, 0.12 mmol) is dissolved in 3 ml of acetone and 0.5 ml of 10% phosphoric acid. After stirring 18 hours at room temperature, the solution is diluted with a 10 fold excess of ethyl acetate and washed with saturated sodium chloride. Purification of the crude phenol (42 mg) by PLC (35% acetone/toluene) provides 2,2-dimethyl-3α-cyano-6α-(p-hydroxy-α-hydroxybenzyl)penam.

The 6β-tetrahydropyranyl ether is deprotected in the same manner to provide 2,2-dimethyl-3α-cyano-6α-(p-hydroxy-α-hydroxybenzyl)penam.

EXAMPLE 23

Activated mossy zinc (1.0 g) and zinc dust (1.2 g) is added to a solution of 2,2-dimethyl-3α-cyano-6α-bromopenam (1.0 g, 3.85 mmol) and p-diphenylmethoxycarbonylbenzaldehyde (1.96 g, 6.2 mmol) in 6 ml of THF (distilled from calcium hydride). After stirring vigorously at room temperature for 18 hours, the mixture is diluted with ethyl acetate. Phosphate buffer (pH 5, 5 ml) is then added. After stirring for 10 min., the solids are removed by filtration and washed thoroughly with ethyl acetate. The layers of the filtrate are separated and the organic phase is washed with phosphate buffer and saturated sodium chloride. Drying with sodium sulfate and solvent removal provides a yellow foam.

Purification of the crude mixture on 60 g of silica gel 60 with 5% acetone/toluene as eluant affords 2,2-dimethyl-3α-cyano-6α-(p-diphenylmethoxycarbonyl-α-hydroxybenzyl)penam and 2,2-dimethyl-3α-cyano-6β-(p-diphenylmethoxycarbonyl-α-hydroxybenzyl)penam.

EXAMPLE 24

2,2-Dimethyl-3α-cyano-6α-(p-diphenylmethoxycarbonyl-α-hydroxybenzyl)penam (0.26 mmol, 132 mg) is dissolved in 1.2 ml of anisol and cooled to 0°. Dry trifluoroacetic acid (3 ml) is added and the solution is allowed to stand at 0° for 2 mins. The trifluoroacetic acid is removed under high vacuum at 0° and the anisol is distilled off at 30°. More anisol is added and distilled off. This is again repeated and the oily residue partitioned between 5 ml of cold water containing 22 mg of sodium bicarbonate and ether. The phases are separated and the aqueous phase is again washed with ether and lyophilized, affording sodium 2,2-dimethyl-3α-cyano-6α-(p-carboxy-α-hydroxybenzyl)penam.

2,2-dimethyl-3α-cyano-6β-(p-diphenylmethoxycarbonyl-α-hydroxybenzyl)penam (62 mg, 0.12 mmol) is treated in the same manner to provide sodium 2,2-dimethyl-3α-cyano-6β-(p-carboxy-α-hydroxybenzyl)penam.

What is claimed is:

1. The process for preparing and isolating a β-lactam having a substituted hydroxymethylene group at the position α to the lactam carbonyl group of the following formulae:

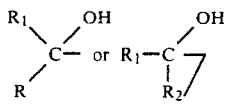

wherein R and $R_1$ together with the carbon atom to which they are attached is the carbon residue of an aldehyde or ketone which contains no functional group that would preferentially react with a zinc halo-β-lactam intermediate over the oxo functionality;
and wherein $R_2$ is a group of the formula $$-(CH_2)_m-X_p-(CH_2)_n-$$

wherein X is O or S; m is 0-3; n is 0-3; p is 0-1; with the proviso that that m+n+p is 3-5;
which comprises the reaction of an α-halo-β-lactam wherein halo is chlorine, bromine or iodine, with zinc or zinc amalgam in an anhydrous aprotic medium at temperatures in the range of from about 0° C. to about 110° C., in the presence of an appropriate aldehyde or ketone, and breaking the zinc complex by the addition of water or a buffer of PH of about 5-7.

2. The process of claim 1 wherein the halo-β-lactam is of the formula

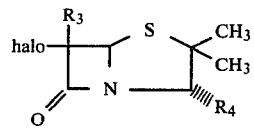

wherein halo is a halogen selected from the group consisting of chlorine, bromine or iodine, $R_3$ is hydrogen or lower alkoxy, and $R_4$ is cyano or $COOR_{11}$ wherein $R_{11}$ is a readily removable esterforming moiety.

3. The process of claim 1 wherein the halo-β-lactam is of the formula

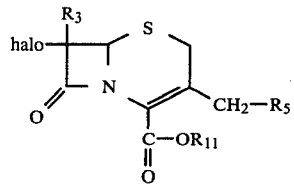

wherein halo is a halogen selected from the group consisting of chlorine, bromine or iodine, $R_3$ is hydrogen or lower alkoxy, and $R_1$ is a readily removable ester-forming moiety, $R_5$ is hydrogen, lower alkanoyloxy, lower alkoxy, lower alkylthio, pyridinium,

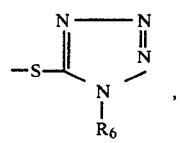

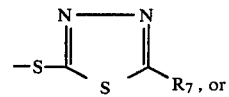

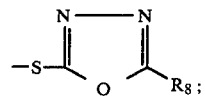

wherein $R_6$, $R_7$ and $R_8$ are hydrogen, lower alkyl, phenyl, lower alkylphenyl, halophenyl, hydroxyphenyl, lower alkoxyphenyl, or

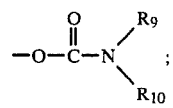

wherein $R_9$ and $R_{10}$ can be the same or different and are hydrogen or lower alkyl.

4. The process of claim 1 wherein the halo-β-lactam is of the formula:

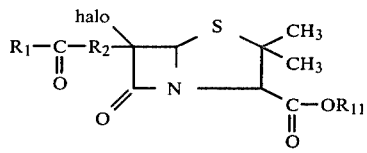

wherein halo is a halogen atom selected from the group consisting of chlorine, bromine or iodine, $R_{11}$ is a readily removable ester-forming moiety,

is an attached keto or aldehyde functional group, $R_2$ is a group of the formula $$-(CH_2)_m-X_p-(CH_2)_n$$

wherein X is O or S; m is 0-3; n is 0-3; p is 0-1; with the proviso that m+n+p is 3-5.

5. The process of claim 1 wherein the halo-β-lactam is of the formula

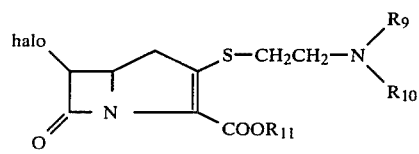

wherein halo is a halogen atom selected from the group consisting of chlorine, bromine or iodine, $R_9$ and $R_{10}$ can be the same or different and/or hydrogen, or lower alkyl, and $R_{11}$ is a readily removable ester-forming moiety.

6. The process of claim 1 wherein the halo-β-lactam is of the formula

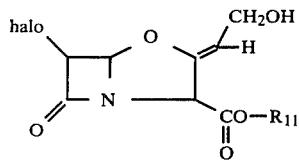

wherein halo is selected from the group consisting of chlorine, bromine or iodine, and $R_{11}$ is a readily removable ester-forming moiety.

7. The process of claim 1 wherein activated zinc is utilized.

8. The process of claim 7 wherein the solvent is tetrahydrofuran.

9. The process of claim 2 wherein the halo-β-lactam is methyl-6α-bromopenicillanate.

10. The process of claim 2 wherein the halo-β-lactam is benzhydryl-6α-bromopenicillanate.

11. The process of claim 2 wherein the halo-β-lactam is benzyl-6β-bromo-6α-methoxypenicillanate.

12. The process of claim 2 wherein the halo-β-lactam is 2,2-dimethyl-3α-cyano-6α-bromopenam.

13. The process of claim 3 wherein the halo-β-lactam is benzhydryl 7α-bromocephalosporanate.

14. The process of claim 4 wherein the halo-β-lactam is 6α-oxopropoxy-6β-bromopenicillanate.

* * * * *

UNITED STATES PATENT AND TRADEMARK OFFICE
CERTIFICATE OF CORRECTION

PATENT NO. : 4,283,531
DATED : 8/11/81
INVENTOR(S) : Ashit K. Ganguly, Viyyoor M. Girijavallabhan, Patricia Cavender, Olga Sarre, Stuart W. McCombie.

It is certified that error appears in the above-identified patent and that said Letters Patent are hereby corrected as shown below:

Column 22, line 39, "$R_1$" should read ---$R_{11}$---.

Signed and Sealed this

Seventeenth Day of November 1981

[SEAL]

Attest:

GERALD J. MOSSINGHOFF

Attesting Officer

Commissioner of Patents and Trademarks